United States Patent [19]
Sohn et al.

[11] Patent Number: 5,998,648
[45] Date of Patent: Dec. 7, 1999

[54] ANTICANCER (IV) COMPLEXES FOR ORAL ADMINISTRATION AND A METHOD OF MAKING THE SAME

[75] Inventors: Youn Soo Sohn, Seoul; Sung Sil Lee, Kuri; Young-A Lee; Kwan Mook Kim, both of Seoul; Chong Ock Lee, Daejon, all of Rep. of Korea

[73] Assignee: Korea Institute of Science and Technology, Seoul, Rep. of Korea

[21] Appl. No.: 09/134,697

[22] Filed: Aug. 14, 1998

[30] Foreign Application Priority Data

Dec. 30, 1997 [KR] Rep. of Korea ............... 97-79743

[51] Int. Cl.$^6$ ..................................... C07F 15/00
[52] U.S. Cl. ..................... 556/137; 556/136; 549/206
[58] Field of Search ................... 556/137, 136; 549/206

[56] References Cited

U.S. PATENT DOCUMENTS

| | | | |
|---|---|---|---|
| 4,937,358 | 6/1990 | Bitha | 549/206 |
| 4,996,337 | 2/1991 | Bitha | 556/137 |
| 5,072,011 | 12/1991 | Abrams | 556/137 |
| 5,288,887 | 2/1994 | Khokhar | 556/137 |
| 5,648,384 | 7/1997 | Kidani | 556/137 |

FOREIGN PATENT DOCUMENTS

| | | |
|---|---|---|
| 0 328 274 A1 | 8/1989 | European Pat. Off. |
| 0 646 589 A2 | 4/1995 | European Pat. Off. |

OTHER PUBLICATIONS

Leh, F. (1976) "Journal of Organic Chemistry", *Journal of Pharmaceutical Sciences*, vol. 65:3.

Leo, A. (1971) "Partition Coeffients and Their Uses", *Chemical Reviews*, vol. 71:6.

Ellis, L. (1995), "The Influence of the Axial Ligands of a Series of Platinum (IV) Anti–Cancer Complexes on their Reduction to Platinum (II) and Reaction with DNA", *Aus. J. Chem.* vol. 48:793–806 (Excerpt).

Galanski, M. (1996) "Carboxylation of Dihydroxoplatinum (IV) Complexes via a New Synthetic Pathway", *Inorg. Chem.*, vol. 35:1709–1711.

Giandomenico, C. (1995) "Articles", *Inorganic Chemistry*, vol. 34:1015–1021 (Excerpt).

Harrison, R.C. (1980) "An Efficient Route for the Preparation of Highly Soluble Platinum (II) Antitumor Agents", *Inorganica Chimica Acta*, vol. 46:L15–L16.

*Primary Examiner*—Gary Geist
*Assistant Examiner*—Jean F Vollano
*Attorney, Agent, or Firm*—Scully, Scott, Murphy & Presser

[57] ABSTRACT

Platinum (IV) complexes for oral administration represented by the structural formula

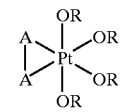

where A—A is a symmetrical diamine that can chelate to platinum and is selected from the group consisting of ethylene diamine, t(±)-1,2-diaminocyclohexane, 2,2-dimethyl-1,3-propanediamine, cyclohexane-1,1-dimethaneamine and tetrahydro-4H-pyran-4,4-dimethaneamine; and R is propionyl, butyryl or valeryl. These complexes are useful in the treatment of cancer.

6 Claims, No Drawings

ANTICANCER (IV) COMPLEXES FOR ORAL ADMINISTRATION AND A METHOD OF MAKING THE SAME

BACKGROUND OF THE INVENTION

The present invention relates to anticancer platinum(IV) complexes for oral administration and a preparation method thereof. More particularly, the present invention relates to lipophilic platinum(IV) complexes. which are potent anticancer agents when administered orally, represented by Formula I and a preparation method thereof.

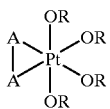
(I)

(wherein A—A is a symmetric diamine that can chelate to platinum and is selected from the group consisting of ethylene diamine $(NH_2CH_2CH_2NH_2)$, t($\pm$)-1,2-diaminocyclohexane

2,2-dimethyl-1,3-propanediamine $(NH_2CH_2C(CH_3)_2CH_2NH_2)$, cyclohexane-1.1-dimethanamine

and tetrahydro-4H-pyran-4.4-dimethanamine $(O(CH_2CH_2)_2C(CH_2NH_2)_2)$, and an anionic group R is selected from the group consisting of propionyl $(C_2H_5CO)$, butyryl $(C_3H_7CO)$ and valeryl $(C_4H_9CO)$ groups.

The present inventors have found that the platinum(IV) complexes which contain one of the symmetric diamines above and four identical carboxylic groups can be easily absorbed in the gastrointestinal track due to their high lipophilicity, and thus are potent oral anticancer drugs. The only two platinum complexes that are currently in clinical use are cisplatin (cis-$(NH_3)_2PtCl_2$), and carboplatin

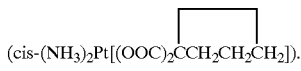

These platinum complexes are administered via injection, and orally administrable anticancer drugs have not yet been developed. Moreover, despite the high anticancer activity of these platinum (II) complexes for injection, their use is limited due to their severe side effects, such as nephrotoxicity and neurotoxicity (F. K. V. Leh, et. al, *J. Pharm. Sciences*, 65, 315 (1976)). Furthermore, these platinum (II) complexes for injection exhibit narrow therapeutic spectrum and cross-resistance. Therefore, a great deal of efforts have been made to develop the third generation anticancer drug for oral administration which show a wider therapeutic specturm and no cross-resistance. To date, however, such efforts have not been successful. Recently, researches are actively underway to find orally active platinum(IV) anticancer drugs. The oral route is preferred to injection since not only oral administration is presumed to reduce the side effects due to cytotoxicity resulting from injection of the drug, but also, it is more convenient and cost-effective for patients since they do not have to be hospitalized for treatment. Despite the need for such oral anticancer drugs, development has not been successful because some strict requirements should be satisfied. First of all, the oral anticancer drug must be chemically stable in the highly acidic (pH=1–2) environment of the stomach, and secondly, it must be well absorbed in the gastro-intestinal track. Most of the 4-coordinate platinum (II) complexes do not satisfy these requirements, and only 6-coordinate platinum(IV) complexes can be considered as a possible oral anticancer agent (C. M. Giadomenico et.al., Inorg. Chem. 34, 1015 (1995)). Thirdly, the oral platinum (IV) anticancer drugs must have an appropriate reduction properties since they need to be reduced to a platinum (II) complex to combine with deoxyribonucleic acid (DNA) in the cell (L. T. Ellis et. al., *Aust. J. Chem.* 48 793 (1995)). Therefore, despite the efforts, the 6-coordinate platinum (IV) complex anticancer agents have not been commercialized to date. Only JM216 (cis, trans,

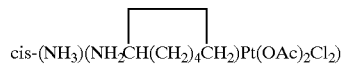

(M. Abrams, European patent pending 89300787.2) developed by Johnson-Matthey of Great Britain is in the clinical phase II study and Cn-OHP (cis, trans,

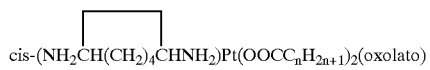

(Y. Kidany, European patent pending 94202874.7) of the Kidany's group in Japan is in preparation for clinical studies.

The conventional method for preparation of preparing the 6-coodinate platinum(IV) complexes is to first synthesize 4-coordinate platinum(II) complexes which are expected to have anticancer activity, and oxidize them by using hydrogen peroxide or halogens. Then the newly added axial ligands, that is hydroxyl or halide (such as chloride and bromide) groups are substituted with a different ligand such as carboxylate groups (C. M. Giandomenico et. al., *Inorg. Chem.* 34, 1015 (1995)). Such conventional oxidative addition reaction for the 6-coordinate platinum(IV) complexes can afford only variation of the axial ligands. And moreover, such nucleophilic substitution is known to be very difficult because of the intrinsic inertness of metal-ligand bonds in the octahedral platinum(IV) complexes (M. Galanski et. al., *Inorg. Chem.* 1996, 35, 1709).

SUMMARY OF THE INVENTION

It is an object of the present invention to develop new platinum complexes that are efficient anticancer agents when administered orally.

More particularly, it is an object of the present invention to develop anticancer platinum(IV) complexes for oral administration.

Another object of the present invention is to provide a method of preparing anticancer platinum(IV) complexes for oral administration.

While exploring the synthetic schemes for various 6-coordinate platinum(IV) complexes, we, the inventors have found that 6-coordinate platinum(IV) complexes can be prepared by first preparing an intermediate, (diamine) tetrahydroxyplatinum(IV) $(A_2Pt(OH)_4)$, by oxidizing a 4-coodinate (diamine)platinum(II) complex with hydrogen peroxide and then by synthesizing the 6-coordinate platinum (IV) complexes by substituting the four hydroxy groups via electrophilic substitution reaction. Especially, the platinum (IV) complexes of Formula I where the four hydroxy groups were substituted with acyl groups were efficient anticancer agents (see Table 1) since they were more lipophilic than the existing platinum(IV) complexes, such as $A_2PtCl_2(OR)_2$ or a un-acylated intermediate, $A_2Pt(OH)_4$.

The manner in which the foregoing and other objects of this invention are accomplished will be apparent from the accompanying specification and claims considered together with the working examples.

DETAILED DESCRIPTION OF THE INVENTION

The preparation method of the platinum(IV) complexes of Formula I is as follows. Potassium tetrachloroplatinum ($K_2PtCl_4$), potassium iodide (KI) and corresponding amine were reacted as described in the literature (R. C. Harrison, et. al, Inorg. *Chimica Acta*, 46, L15 (1980)) to obtain (diamine)platinum(II) iodide of Formula II, which was reacted with the same equivalent of silver sulfate or silver nitrate for 5 hours at room temperature to obtain water soluble (diamine)platinum(II) sulfate or nitrate of Formula III or Formula IV, respectively.

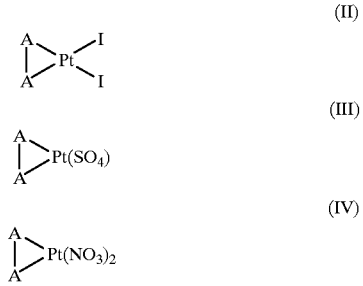

(In the above Formulas, A—A is identical to the A—A of Formula I)

To (diamine)platinum(II) sulfate or nitrate of Formula III or Formula IV, respectively, 50 to 100% excess amount, i.e., 1.5 to 2.0 equivalent of 30% aqueous hydrogen peroxide solution was added and the reaction mixture was stirred for 2 hours at room temperature. The sulfate or nitrate anion was removed by using an anion exchange column, and then the solution was evaporated to obtain platinum(IV) hydroxide of Formula V. In case of (diamine)platinum(II) sulfate of Formula III, it is also possible to obtain the platinum(IV) hydroxide crystals of Formula V by using an exact amount of barium hydroxide ($Ba(OH)_2 \cdot 8H_2O$) equivalent to platinum(II) to remove the sulfate ion as the barium sulfate form instead of using an anionic exchange column,

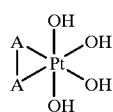

(In the above Formula, A—A is identical to the A—A of Formula I)

White or pale yellow crystalline products of the 6-coordinate platinum(IV) complex of Formula I were obtained as follows. An intermediate, (diamine)platinum (IV) hydroxide of Formula V is dispersed directly in a neat carboxylic anhydride and reacted for 5 to 10 hours at room temperature to obtain the 6-coordinate platinum(IV) complexes of Formula I. Another method of obtaining the 6-coordinate platinum(IV) complex of Formula I is, first, to disperse the (diamine)platinum(IV) hydroxide of Formula V into a polar solvent such as dichloromethane or acetone, and to this solution, 6 to 10 equivalent carboxylic anhydride ($R_2O$) or acyl chloride (RCI) per mole of (diamine)platinum (IV) hydroxide of Formula V is added for reaction for 5–10 hours at room temperature or below 60° C. The white or pale yellow crystalline powders of the 6-coordinate platinum(IV) complexes of Formula I are obtained when an excess amount of a nonpolar organic solvent, such as diethylether or n-hexane, is added. Especially when the (diamine) platinum(IV) hydroxide of Formula V is reacted with acyl chloride (RCI). the reaction should be performed in the presence of a hydrogen chloride removing agent such as pyridine or triethylamine at 30~60° C. The preparation procedure of the present invention can be described as in the following reaction Scheme.

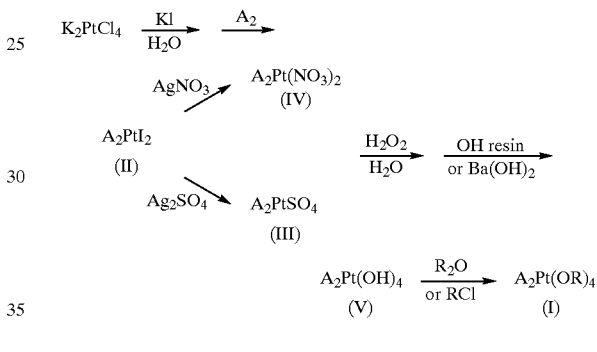

The invention will be further illustrated by the following examples, but not limited to the examples given.

The elemental analysis for the platinum complexes of the present invention was performed in the Chemical Analysis Center at Korea Institute of Science and Technology by using a CHN analyzer (Perkin Elmer). The infrared spectra of the samples were obtained as KBr pellet by Perkin Elmer 16F PC Ft-IR in the range of 4000 and 400 $cm^{-1}$.

EXAMPLE 1.

Preparation of [t(±)-$NH_2CH(CH_2)_4CHNH_2$]Pt($OOCC_2H_5$)$_4$

EXAMPLE 1.

Preparation of [t(±)-$NH_2CH(CH_2)_4CHNH_2$]Pt($OOCC_2H_5$)$_4$ (A—A = t(±)- $NH_2CH(CH_2)_4CHNH_2$; R = $C_2H_5CO$)

To an aqueous solution containing 6.23 g (15.0 mmole) of $K_2PtCl_4$, 12.45 g (75 mmol) of potassium iodide was added. After the reaction mixture was stirred for 30 min., 20 ml of an aqueous solution containing 2.06 g (18 mmol) trans (±)-1,2-diaminocyclohexane was slowly added and the reaction mixture was stirred for 3 hours. The yellow precipitate was filtered, washed with distilled water 3 times (30 ml×3) and dried under reduced pressure at warm temperature (3 mmHg, 40° C.) to obtain 7.47 g (yield, 88.5%) of

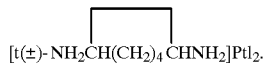

After 5.63 g (10.0 mmol) of

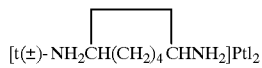

and 3.40 g (20.0 mmol) of AgNO$_3$ are reacted in 200 ml of distilled water for 5 hours. the AgI precipitate formed was filtered out to obtain an aqueous solution of

An excess amount of 30% aqueous hydrogen peroxide solution was added to the

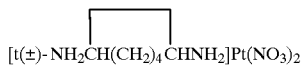

solution, which was stirred for 5 hours. After filtering out a small amount of precipitate, the filtrate was concentrated to a total volume of 100 ml under reduced pressure at warm temperature (3 mm Hg, 40° C.). The condensed aqueous solution was passed through a glass column containing anionic resin (OH$^{31}$ type, 100 ml), which was eluted by 400 ml of distilled water. The total aqueous solution (500 ml) that passed through the anionic resin was dried under reduced pressure at warm temperature (3 mm Hg, 40° C.) to obtain 2.43 g (yield, 64.3%) of [t(±)-NH$_2$CH(CH$_2$)$_4$CHNH$_2$]Pt(OH)$_4$.

To a solution of 1.00 g (2.65 mmol) of

dispersed in 25 ml of dichloromethane, 6.4 ml (50.0 mmol) of propionic anhydride was added, and the reaction mixture was stirred for 8 hours at room temperature. The product was precipitated by adding an excess amount of diethylether (60 ml). The precipitate was filtered and washed twice (15 ml×2) with diethylether under reduced pressure (3 mm Hg) at room temperature to obtain 0.89 g (yield, 55.8%) of the platinum complex,

Melting point: 169° C. (decomposition)
Molecular formula: (C$_{18}$H$_{34}$N$_2$O$_8$)Pt
Elemental analysis: C, 36.2; H, 5.73; N, 4.54
Theoretical value: C, 35.9; H, 5.70; N, 4.66
Infrared absorbance bands (KBr cm$^{-1}$): 642(m), 700(m), 1032(m), 1152(m), 1273(s), 1344(s), 1456(m), 1632(s), 2884(m), 2940(m), 3102(m), 3448(m)

EXAMPLE 2.

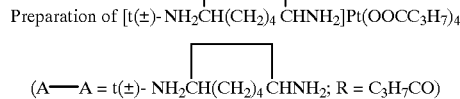

One gram (2.65 mmol) of

prepared by using the same procedure as described in Example 1 and 4.1 ml (25.0 mmol) of butyric anhydride were used to prepare 0.91 g (yield, 49.3%) of

using the same method as described in Example 1.
Melting point: 174° C. (decomposition)
Molecular formula: (C$_{22}$H$_{42}$N$_2$O$_8$)Pt(2H$_2$O)
Elemental analysis: C, 38.3; H, 6.65; N, 4.01
Theoretical value: C, 38.1; H, 6.68; N, 4.04
Infrared absorbance bands (KBr cm$^{-1}$): 636(m), 696(m), 1048(m), 1156(m), 1297(s), 1366(m), 1392(s), 1481(m), 1627(s), 2848(m), 2987(s), 3127(m), 3452(m)

EXAMPLE 3.

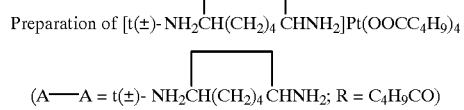

One gram (2.65 mmol) of

prepared by using the same procedure as described in Example 1, and 4.9 ml (25.0 mmol) of valeric anhydride were used to prepare 1.11 g (yield, 57.2%) of

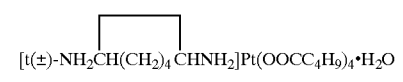

by using the same method as described in Example 1.
Melting point: 183° C. (decomposition)
Molecular formula: (C$_{26}$H$_{50}$N$_2$O$_8$)Pt(H$_2$O)
Elemental analysis: C, 42.5; H, 7.18; N, 3.81
Theoretical value: C, 42.7; H, 7.16; N, 3.83
Infrared absorbance bands (KBr cm$^{-1}$): 574(m), 702(m), 1062(m), 1086(m), 1143(m), 1282(s), 1396(s), 1447(m), 1492(m), 1622(s), 2836(m), 2976(s), 3224(m), 3446 (m)

EXAMPLE 4

Preparation of $(NH_2CH_2CH_2NH_2)Pt(OOCC_3H_7)_4$
$(A-A=NH_2CH_2CH_2NH_2; R=C_3H_7CO)$ By following the same procedure as in Example 1, 6.96 g (yield, 91.2%) of $(NH_2CH_2CH_2NH_2)PtI_2$ was obtained using the same equivalent of ethylenediamine instead of $t(\pm)$-1,2-diaminocyclohexane.

After reaction of 5.09 g (10.0 mmol) of $(NH_2CH_2CH_2NH_2)PtI_2$ and 3.12 g (10.0 mmol) of $Ag_2SO_4$ in distilled water for 5 hours, the AgI precipitate formed was filtered out to obtain an aqueous solution of $(NH_2CH_2CH_2NH_2)PtSO_4$. An excess amount of 30% aqueous hydrogen peroxide solution (5 ml) was added to the $(NH_2CH_2CH_2NH_2)PtSO_4$ solution, which was stirred for 4 hours. After filtering out a small amount of precipitate, the filtrate was concentrated to a total volume of 50 ml under reduced pressure at warm temperature (3 mm Hg, 40° C.). 20 ml of an aqueous solution containing 3.15 g (10.0 mmol) of barium hydroxide $(Ba(OH)_2.8H_2O)$ was added to this concentrated solution and the reaction mixture was stirred for 3 hours. After filtering out the precipitate($BaSO_4$), the filtrate was evaporated under reduced pressure at warm temperature (3 mm Hg, 40° C.) to obtain 1.57 g (yield, 48.6%) of $(NH_2CH_2CH_2NH_2)Pt(OH)_4$.

One gram (3.1 mmol) of $(NH_2CH_2CH_2NH_2)Pt(OH)_4$ was dispersed in 10 ml (61.0 ml) of butyric anhydride, and the mixture was stirred for 8 hours at room temperature until the solid reactant was completely dissolved. The carboxylated product was precipitated by adding an excess amount of diethylether (100 ml). The precipitate was filtered, washed twice (15 ml×2) with diethylether, and dried under reduced pressure (3 mm Hg) at room temperatures (25° C.) to obtain 0.86 g (yield, 46.0%) of the platinum complex, $(NH_2CH_2CH_2NH_2)Pt(OOCC_3H_7)_4$.

Melting point: 182° C. (decomposition)
Molecular formula: $(C_{18}H_{36}N_2O_8)Pt$
Elemental analysis: C, 35.5; H, 5.97; N, 4.62
Theoretical value: C, 35.8; H, 6.01; N, 4.64
Infrared absorbance bands (KBr cm$^{-1}$): 582(m), 670(m), 1062(m), 1176(m), 1212(s), 1288(s), 1360(s), 1452(m), 1638(m), 2678(m), 2964(m), 3230(m), 3448(m)

EXAMPLE 5

Preparation of $(NH_2CH_2CH_2NH_2)Pt(OOCC_4H_9)_4$
$(A-A=NH_2CH_2CH_2NH_2; R=C_4H_9CO)$ One gram (3.10 mmol) of $(NH_2CH_2CH_2NH_2)Pt(OH)_4$ prepared by using the procedure described in Example 4, and 4.9 ml (25.0 mmol) of valeric anhydride were used to prepare 1.07 g (yield, 52.5%) of $(NH_2CH_2CH_2NH_2)Pt(OOCC_4H_9)_4$ by using the same method as described in Example 4.

Melting point: 194° C. (decomposition)
Molecular formula: $(C_{22}H_{44}N_2O_8)Pt$
Elemental analysis: C, 40.0; H, 6.75; N, 4.28
Theoretical value: C, 40.1; H, 6.72; N, 4.25
Infrared absorbance bands (KBr cm$^{-1}$): 614(m), 712(m), 934(m), 1018(m), 1180(m), 1282(s), 1347(s), 1364(s), 1648(s), 2880(m), 2971(s), 3223(m), 3442(m)

EXAMPLE 6

Preparation of $[NH_2CH_2C(CH_3)_2CH_2NH_2]Pt(OOCC_2H_5)_4$
$(A-A=NH_2CH_2C(CH_3)_2CH_2NH_2; R=C_2H_5CO)$ To an aqueous solution (150 ml) containing 6.23 g (15.0 mmol) of $K_2PtCl_4$, 12.45 g (75 mmol) of potassium iodide was added. After stirring the mixture for 30 minutes, 1.84 g (18 mmol) of 2,2-dimethyl-1,3-propanediamine was slowly added and the reaction mixture was stirred for 3 hours. The yellow precipitate formed was filtered, washed three times (30 ml×3) with distilled water and dried under reduced pressure at warm temperature (3 mmHg, 40° C.) to obtain 7.50 g (yield, 90.7%) of $[NH_2CH_2C(CH_3)_2CH_2NH_2]PtI_2$.

By following the same procedure as in Example 4, 2.10 g (yield, 57.5%) of $[NH_2CH_2C(CH_3)_2CH_2NH_2]Pt(OH)_4$ was obtained using the same equivalent of $[NH_2CH_2C(CH_3)_2CH_2NH_2]PtI_2$ instead of $[NH_2CH_2CH_2NH_2]PtI_2$.

By reaction of 1.00 g (2.74 mmol) of $[NH_2CH_2C(CH_3)_2CH_2NH_2]Pt(OH)_4$ and 6.4 ml (50.0 mmol) of propionic anhydride in the same way as in Example 4, 1.00 g (yield, 62.1%) of $[NH_2CH_2C(CH_3)_2CH_2NH_2]Pt(OOCC_2H_5)_4$ was obtained.

Melting point: 187° C. (decomposition)
Molecular formula: $(C_{17}H_{34}N_2O_8)Pt$
Elemental analysis: C, 34.8; H, 5.80; N, 4.77
Theoretical value: C, 34.6; H, 5.81; N, 4.75
Infrared absorbance bands (KBr cm$^{-1}$): 632(m), 700(m), 802(m), 1047(m), 1138(m), 1237(m), 1382(s), 1467(m), 1618(s), 1632(s), 2893(m), 2944(s), 3135(m), 3407(m)

EXAMPLE 7

Preparation of $[NH_2CH_2C(CH_3)_2CH_2NH_2]Pt[OOCCH(CH_3)_2]_4$
$(A-A=NH_2CH_2C(CH_3)_2CH_2NH_2; R=(CH_3)_2CHCO)$ One gram (2.74 mmol) of $[NH_2CH_2C(CH_3)_2CH_2NH_2]Pt(OH)_4$ prepared by using the procedure described in Example 6 and 4.1 ml (25.0 mmol) of isobutyric anhydride were used to prepare 0.78 g (yield, 42.7%) of $[NH_2CH_2C(CH_3)_2CH_2NH_2]Pt(OOCCH(CH_3)_2)_4 \cdot H_2O$ using the same method as described in Example 6.

Melting point: 191° C. (decomposition)
Molecular formula: $(C_{21}H_{42}N_2O_8)Pt(H_2O)$
Elemental analysis: C, 37.8; H, 6.65; N, 4.16
Theoretical value: C, 38.0; H, 6.68; N, 4.22
Infrared absorbance bands (KBr cm$^{-1}$): 614(m), 696(m), 1042(m), 1256(m), 1297(m), 1367(m), 1397(s), 1458(m), 1637(s), 2948(m), 3133(m), 3221(m), 3448(m)

EXAMPLE 8

Preparation of $[O(CH_2CH_2)_2C(CH_2NH_2)_2]Pt(OOCC_2H_5)_4$
$(A-A=O(CH_2C_2)_2C(CH_2NH_2)_2; R=C_2H_5CO)$ The same equivalent of tetrahydro-4H-pyran-4,4-dimethanamine was used instead of $t(\pm)$-1,2-diaminocyclohexane to prepare 7.62 g (yield, 85.6%) of $[O(CH_2CH_2)_2C(CH_2NH_2)_2]PtI_2$ using the same procedure as described in Example 1.

The same equivalent of $[O(CH_2CH_2)_2C(CH_2NH_2)_2]PtI_2$ was used instead of $[t(\pm)$-$NH_2CH(CH_2)_4CHNH_2]PtI_2$ to prepare 2.55 g (yield, 62.5%) of $[O(CH_2CH_2)_2C(CH_2NH_2)_2]Pt(OH)_4$ using the same procedure as described in Example 1.

One gram (2.45 mmol) of $[O(CH_2CH_2)_2C(CH_2NH_2)_2]Pt(OH)_4$ and 6.4 ml (50.0 mmol) of propionic anhydride were reacted to prepare 0.81 g (yield 50.6%) of $[O(CH_2CH_2)_2C(CH_2NH_2)_2]Pt(OOCC_2H_5)_4 \cdot H_2O$ using the same method as described in Example 1.

Melting point: 194° C. (decomposition)
Molecular formula: $(C_{19}H_{36}N_2O_9)Pt(H_2O)$
Elemental analysis: C, 35.4; H, 5.90; N, 4.33
Theoretical value: C, 35.1; H, 5.90; N, 4.31
Infrared absorbance bands (KBr cm$^{-1}$): 603(m), 695(m), 1036(m), 1135(m), 1162(m), 1257(m), 1345(m), 1382(s), 1447(m), 1612(s), 2940(s), 3092(m), 3216(m), 3435(m)

EXAMPLE 9

Preparation of [O(CH$_2$CH$_2$)$_2$C(CH$_2$NH$_2$)$_2$]Pt(OOCC$_3$H$_7$)$_4$
(A—A=O(CH$_2$CH$_2$)$_2$C(CH$_2$NH$_2$)$_2$; R=C$_3$H$_7$CO)

One gram (2.45 mmol) of [O(CH$_2$CH$_2$)$_2$C(CH$_2$NH$_2$)$_2$]Pt(OH)$_4$ obtained by using the same procedure as in Example 8 and 4.1 ml (25.0 mmol) of butyric anhydride were reacted to prepare 0.79 g (yield, 46.7%) of [O(CH$_2$CH$_2$)$_2$C(CH$_2$NH$_2$)$_2$]Pt(OOCC$_3$H$_7$)$_4$ using the same as described in Example 8.

Melting point: 201° C. (decomposition)
Molecular formula: (C$_{23}$H$_{44}$N$_2$O$_9$)Pt
Elemental analysis: C, 40.0; H, 6.42; N, 4.09
Theoretical value: C, 40.2; H, 6.45; N, 4.07
Infrared absorbance bands (KBr cm$^{-1}$): 612(m), 752(m), 838(m), 1147(m), 1220(m), 1347(s), 1376(s), 1432(m), 1635(s), 2778(m), 2972(s), 3324(m), 3440(m)

EXAMPLE 10.

Preparation of 

(A——A = t(±)-CH(CH$_2$)$_4$C(CH$_2$NH$_2$)$_2$; R = C$_2$H$_5$CO)

The same equivalent of cyclohexane-1,1-dimethanamine was used instead of t(±)-1,2-diaminocyclohexane to prepare 8.22 g (yield, 92.7%) of

using the same procedure as described in Example 1.

The same equivalent of

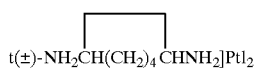

was used instead of t(±)-NH$_2$CH(CH$_2$)$_4$CHNH$_2$]PtI$_2$ prepare 2.14 g (yield, 52.8%) of

using the same procedure as described in Example 1.

After 1.00 g (2.47 mmol) of

and 1.62 ml (20.0 mmol) of pyridine were dispersed in 25 ml of acetone, 0.87 ml (10.0 mmol) of propionyl chloride was added to the mixture, which was stirred for 8 hours at 60° C. After the reaction mixture was cooled to room temperature (25° C.), the product was precipitated by adding an excess amount of diethylether (100 ml). The precipitate was filtered, washed twice (15 ml×2) with diethyl ether and dried under reduced pressure (3 mmHg) at room temperature (25° C.) to obtain 0.81 g (yield, 49.4%) of the platinum complex

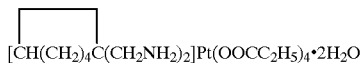

Melting point: 189° C. (decomposition)
Molecular formula: (C$_{20}$H$_{88}$N$_2$O$_8$)Pt(2H$_2$O)
Elemental analysis: C, 36.0; H, 6.32; N, 4.25
Theoretical value: C, 36.1; H, 6.36; N, 4.21
Infrared absorbance bands (KBr cm$^{-1}$): 597(m), 691(m), 846(m), 1135(m), 1287(s), 1348(s), 1398(m), 1467(m), 1647(s), 2893(m), 2988(s), 3105(m), 3451(m)

Oral Anticancer Activity

The oral anticancer activity of the hexa-coordinate platinum(IV) complexes of the present invention was evaluated as follows. A group of eight 6-week old BDF1 mice was employed to test for each compound. 1×10$^5$ cells of L1210 leukemia in ascitic fluid from DBA/2 mice were implanted intraperitoneally in each mouse. The test solutions containing platinum(IV) complexes at different concentrations were orally administered daily for consecutive five days. The survival time of each group of the mice was recorded. The percent increase in the survival time as compared to the control group, T/C (%), was calculated as an indicator of the anticancer activity. The results are summarized in Table I. Drugs that have more than 125% of the T/C (%) values can be considered as efficient anticancer drugs. As shown in Table 1, the platinum (IV) complexes of Example 1 have excellent anticancer activity. It is expected that the complex in Example 1 could be practically applicable since the acute toxicity was also low (LD$_{50}$=300 mg/kg)

TABLE 1

| Platinum complex* | Dose (mg/kg) | Increase ratio in The survival time (T/C, %) | Octanol partition coefficient (P)** |
|---|---|---|---|
| EXAMPLE 1 | 150 | 160.9 | 1.76 |
| EXAMPLE 2 | 150 | 139.1 | 1.90 |
| EXAMPLE 4 | 150 | 115.4 | 1.20 |
| EXAMPLE 6 | 150 | 130.8 | 1.74 |
| EXAMPLE 10 | 150 | 113.5 | 1.15 |
| COMPARATIVE EXAMPLE 1 | 150 | 108.8 | 0.57 |
| COMPARATIVE EXAMPLE 2 | 150 | 103.1 | 0.81 |

*COMPARATIVE EXAMPLE 1: (DACH)Pt(OH)$_4$
COMPARATIVE EXAMPLE 2: (DACH)PtCl$_2$ (OAc)$_4$
**Leo. A. et. al., Chem. Rev. 71, 525 (1971)

According to the present invention, the new platinum(IV) complexes can be administered orally. The platinum(IV) complexes of the present invention, when orally administered, are highly lipophilic, can be absorbed efficiently in the stomach, have excellent anticancer activities and have low toxicity. Moreover, oral anticancer drug is cost-effective and provides convenience to the patients since they can be treated without being hospitalized.

What is claimed is:
1. Platinum (IV) complexes for oral administration having the structural formula

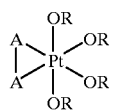

wherein A—A is a symmetrical diamine that can chelate to platinum and is selected from the group consisting of ethylene diamine, t(±)-1,2-diaminocyclohexane, 2,2-dimethyl-1,3-propanediamine, cyclohexane-1,1-dimethanamine and tetrahydro-4H-pyran-4,4-dimethanamine; and R is propionyl, butyryl or valeryl.

2. A method of preparing said platinum (IV) complexes of claim 1 comprising the steps of preparing (diamine)platinum (IV) tetrahydroxide of Formula V,

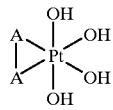

wherein A—A has the meaning given above by direct oxidation of (diamine)-platinum (II) sulfate of Formula III or (diamine)platinum (II) nitrate of Formula IV with hydrogen peroxide,

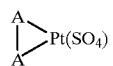

-continued

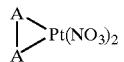

wherein A—A is a symmetrical diamine that can chelate to platinum and is selected from the group selected from the group consisting of ethylene diamine, t(±)-1,2-diaminocyclohexane, 2,2-dimethyl-1,3-propanediamine, cyclohexane-1,1-diamethanamine and tetrahydro-4h-pyran-4,4-dimethanamine, and reacting (diamine)platinum (IV) tetrahydroxide of Formula V with an electrophilic reagent, $R_2O$ or RCl, which is a carboxylic anhydride or acyl chloride, to produce said platinum (IV) complex of claim 1.

3. The method according to claim 2, wherein the (diamine)platinum(IV) tetrahydroxide of Formula V is dispersed in an excess amount of carboxylic anhydride and then precipitated by adding diethylether.

4. The method according to claim 2, wherein the (diamine)platinum(IV) tetrahydroxide of Formula V is dispersed in dichloromethane or acetone solvent and reacted with carboxylic anhydride and then precipitated by adding diethylether.

5. The method according to claim 2, wherein the (diamine)platinum(IV) tetrahydroxide is dispersed in dichloromethane or acetone solvent and reacted with acyl chloride in the presence of hydrogen chloride acceptor and then precipitated by adding diethylether.

6. The method according to claim 4, wherein pyridine is used as a hydrogen chloride acceptor, and the reaction is carried out at 30~60° C. for 5~10 hours.

* * * * *